US007645614B2

(12) United States Patent
Tanaka et al.

(10) Patent No.: US 7,645,614 B2
(45) Date of Patent: Jan. 12, 2010

(54) METHOD OF IMMOBILIZING COMPOUND ON SOLID PHASE SUPPORT

(75) Inventors: Akito Tanaka, Ibaraki (JP); Tomohiro Terada, Ibaraki (JP); Akira Yamazaki, Osaka (JP); Tsuruki Tamura, Ibaraki (JP); Hidenori Nakajima, Ibaraki (JP)

(73) Assignee: Reverse Proteomics Research Institute Co., Ltd., Kisarazu-shi (JP)

( * ) Notice: Subject to any disclaimer, the term of this patent is extended or adjusted under 35 U.S.C. 154(b) by 215 days.

(21) Appl. No.: 10/533,237

(22) PCT Filed: Oct. 31, 2003

(86) PCT No.: PCT/JP03/13974

§ 371 (c)(1),
(2), (4) Date: Apr. 29, 2005

(87) PCT Pub. No.: WO2004/040305

PCT Pub. Date: May 13, 2004

(65) Prior Publication Data

US 2006/0024845 A1 Feb. 2, 2006

(30) Foreign Application Priority Data

Oct. 31, 2002 (JP) ............................. 2002-319099

(51) Int. Cl.
*G01N 33/53* (2006.01)
(52) U.S. Cl. .................. 436/518; 436/514; 436/523; 436/524; 436/532; 436/534; 436/823; 436/824; 435/287.1; 435/287.2
(58) Field of Classification Search .................. 436/514, 436/518, 523, 524, 532, 534, 823, 824; 435/287.1, 435/287.2
See application file for complete search history.

(56) References Cited

U.S. PATENT DOCUMENTS 4,656,144 A 4/1987 Hosaka et al.

| 4,879,340 A | | 11/1989 | Moriguchi et al. |
| 5,578,498 A | * | 11/1996 | Singh et al. .................. 436/518 |
| 6,103,537 A | * | 8/2000 | Ullman et al. ............... 436/526 |

FOREIGN PATENT DOCUMENTS

| EP | 1 265 070 A1 | 12/2002 |
| JP | 57-96260 | 6/1982 |
| JP | 63-48451 | 3/1988 |
| JP | 4-155259 | 5/1992 |
| JP | 11-322799 | 11/1999 |

OTHER PUBLICATIONS

Harding, Matthew W. et al. "A receptor for the immuno-suppressant FK506 is a cis-trans peptidyl-prolyl isomerase", Nature, vol. 341, pp. 758-760 1989.
Liu, Jun et al. "Calcineurin is a Common Target of Cyclophilin-Cyclosporin A and FKBP-FK506 Complexes", Cell, vol. 66, No. 4, pp. 807-815 1991.
Taunton, Jack et al. "A Mammalian Histone Deacetylase Related to the Yeast Transcriptional Regulator Rpd3p", Science, vol. 272, pp. 408-411 1996.
Heinz Fretez, et al., "Rapamycin and FK506 Binding Proteins (Immunophilins)," Journal of the American Chemical Society, American Chemical Society, XP-000310589, vol. 113, No. 4, Feb. 13, 1991, pp. 1409-1411.

* cited by examiner

*Primary Examiner*—Bao-Thuy L Nguyen
(74) *Attorney, Agent, or Firm*—Oblon, Spivak, McClelland, Maier & Neustadt, L.L.P.

(57) ABSTRACT

The present invention provides a method of analyzing the specific interaction between a molecule to be analyzed and a molecule that specifically interacts with the former molecule on a solid phase using a molecule-immobilized solid phase support mixture prepared by binding the subject molecule to the solid phase support without specifying the binding position on the molecule side, particularly a method wherein the immobilization is conducted via a spacer introduced to the molecule without specifying the binding position on the molecule side, which method makes it possible to identify and select only a molecule that exhibits a specific interaction with a molecule to be analyzed, without an investigation of structure-activity correlation, which has conventionally been essential, and hence enables an analysis of the interaction between these molecules.

15 Claims, 3 Drawing Sheets

Lane 1: Marker
Lane 2: Standard affinity resin with FK506 having the binding position established, and proven to be effective (Reference Production Example 3)
Lane 3: Affinity resin with FK506 prepared by binding FK506 directly to resin in the absence of spacer without specifying the position (Example 3)

METHOD OF IMMOBILIZING COMPOUND ON SOLID PHASE SUPPORT

FIELD OF THE INVENTION

The present invention relates to a basic technology for immobilization technique of a compound (subject molecule, especially a low-molecular compound). More specifically, the present invention relates to a technology that enables more efficient immobilization of a subject molecule to a solid phase support in immobilizing the subject molecule to the solid phase support, and measuring an interaction of low-molecular compound and high-molecular compound, low-molecular compound and low-molecular compound or high-molecular compound and high-molecular compound, or purifying a target molecule on the basis of a specific interaction.

BACKGROUND ART

Methods comprising immobilizing a subject molecule (especially a low-molecular compound) to a solid phase support or binding the molecule to another molecule, and measuring a interaction of low-molecular compound and high-molecular compound, low-molecular compound and low-molecular compound or high-molecular compound and high-molecular compound, or purifying a target molecule on the basis of a specific interaction are used successfully in various fields. For example, target protein research using an affinity resin aiming at a novel drug discovery target search is known well. As representative examples of this research, the discovery of FKBP proteins, which bind to the immunosuppressant FK506 (FK506 inding proteins) using an affinity resin by Professor Schreiber in 1989 (discovery of FKBP12 as a protein that binds to FK506 in cells; see, for example, Nature, UK, Oct. 26, 1989, Vol. 341, pp. 758-760), the subsequently done discovery f calcineurin inhibitory action in the mechanism of harmacological action of FK506 by an FK506-FKBP complex (see, or example, Cell, USA, Aug. 23, 1991, Vol. 66, No. 4, pp. 807-815), the discovery of HDAC as a target protein for the anticancer agent Trapoxin (see, for example, Science, USA, Apr. 19, 1996, Vol. 272, pp. 408-411) and the like are known well.

However, to date, to immobilize a low-molecular compound to a solid phase support, it has been necessary to introduce a spacer selectively to a position where the activity is not affected in the low-molecular structure. For this reason, to conduct research for searching and purifying a target molecule, or for analyzing the interaction of a subject molecule and a target thereof, it has been essential to conduct a broad range of research into structure-activity correlation in the subject low-molecular compound in advance, so as to identify a site on the structure at which the desired activity is not lost. However, such investigation has required immense investments and time because it is necessary to synthesize a vast number of compounds separately from each starting material, and to measure the pharmacological activities thereof. Additionally, there are many cases where the desired compound cannot be obtained within the limited time span of research, including some cases where the target search is unavoidably abandoned. Accordingly, the essentially required research into structure-activity correlation has been a major hurdle against the conduct of the above-described research.

In recent years, large investments in genome-based drug discovery have been made for the purpose of effective drug discovery target search; since target search using an affinity resin permits more efficient investments than genome research, a new approach to overcoming the above-described drawback has been waited for.

It is an object of the present invention to provide a method that enables an analysis of intermolecular interactions on a solid phase support, without the need of research into structure-activity correlation, and a search of a target molecule for a subject compound (ligand) on the basis of the analysis.

DISCLOSURE OF THE INVENTION

With the aim of solving the above-described problems, the present inventors devised a method comprising using 1) a functional group that is originally present in a ligand (hereinafter referred to as a functional group intrinsic to ligand), or 2) a functional group newly introduced to a ligand, directly in the immobilization reaction, or indirectly via an appropriate spacer in the immobilization reaction, without investigating the structure-activity correlation for the ligand, and developed a general method of immobilizing a low-molecular compound.

More specifically, the present inventors developed 1) a method of searching a target molecule for a ligand by using a functional group intrinsic to the ligand directly in the immobilization reaction, or indirectly via an appropriate spacer in the immobilization reaction, in a case where an available functional group is originally present in the ligand, and 2) a method of searching a target molecule for a ligand by carrying out a chemical or enzymatic reaction to add a functional group to the ligand, and then using the functional group directly in the immobilization reaction, or indirectly via an appropriate spacer in the immobilization reaction, in a case where no available functional group is present in the ligand.

Accordingly, the present invention relates to:

[1] A method of analyzing the interaction of a molecule A and a molecule B that exhibits a specific interaction with the molecule A, which comprises at least the following steps:
(1) a step of preparing a molecule A-immobilized solid phase support mixture by binding a molecule A to a solid phase support without specifying the binding position on the molecule A side,
(2) a step of bringing a sample containing or not containing a molecule B into contact with the solid phase support mixture prepared in (1) above, and
(3) a step of identifying a molecule that has exhibited or has not exhibited a specific interaction with the molecule A, and analyzing the interaction of the molecule A and the molecule B.

[2] The method described in [1] above, which comprises introducing a spacer between the molecule A and the solid phase support, without specifying the introduction position on the molecule A side, in the step of preparing the molecule A-immobilized solid phase support mixture.

[3] The method described in [1] above, wherein (1) a functional group is introduced to the molecule A, and (2) the introduction of the functional group is conducted without specifying the introduction position on the molecule A side, in the step of preparing the molecule A-immobilized solid phase support mixture.

[4] The method described in [2] above, wherein the introduction of the spacer to the molecule A is conducted via a functional group introduced without specifying the introduction position on the molecule A side.

[5] The method described in [3] or [4] above, wherein the introduction of the functional group to the molecule A without specifying the introduction position on the molecule A side is based on a chemical reaction or an enzymatic reaction.

[6] The method described in [5] above, wherein the introduction of the functional group to the molecule A without specifying the introduction position on the molecule A side is based on an enzymatic reaction.

[7] The method described in [6] above, wherein the enzymatic reaction is conducted using a metabolic enzyme.
[8] A method of selecting a molecule B that exhibits a specific interaction with a molecule A, which comprises at least the following steps:
(1) a step of preparing a molecule A-immobilized solid phase support mixture by binding a molecule A to a solid phase support without specifying the binding position on the molecule A side,
(2) a step of bringing a sample containing or not containing a molecule B into contact with the solid phase support mixture prepared in (1) above, and
(3) a step of identifying a molecule that has exhibited or has not exhibited a specific interaction with the molecule A, and selecting the molecule B.
[9] The method described in [8] above, which comprises introducing a spacer between the molecule A and the solid phase support, without specifying the introduction position on the molecule A side, in the step of preparing the molecule A-immobilized solid phase support mixture.
[10] The method described in [8] above, wherein (1) a functional group is introduced to the molecule A, and (2) the introduction of the functional group is conducted without specifying the introduction position on the molecule A side, in the step of preparing the molecule A-immobilized solid phase support mixture.
[11] The method described in [9] above, wherein the introduction of the spacer to the molecule A is conducted via a functional group introduced without specifying the introduction position on the molecule A side.
[12] The method described in [10] or [11] above, wherein the introduction of the functional group to the molecule A without specifying the introduction position on the molecule A side is based on a chemical reaction or an enzymatic reaction.
[13] The method described in [12] above, wherein the introduction of the functional group to the molecule A without specifying the introduction position on the molecule A side is based on an enzymatic reaction.
[14] The method described in [13] above, wherein the enzymatic reaction is conducted using a metabolic enzyme.
[15] A molecule A-immobilized solid phase support mixture comprising two or more kinds of molecule A-immobilized solid phase supports prepared by binding a molecule A to solid phase supports without specifying the binding position on the molecule A side, wherein said two or more kinds of molecule A-immobilized solid phase supports have the molecule A immobilized thereto at respective different positions on the molecule A.
[16] The molecule A-immobilized solid phase support mixture described in [15] above, wherein the binding of the molecule A to the solid phase support is conducted via a spacer introduced between the molecule A and the solid phase support without specifying the introduction position on the molecule A side.
[17] The molecule A-immobilized solid phase support mixture described in [15] above, wherein (1) the binding of the molecule A to the solid phase support is conducted via a functional group introduced to the molecule A, and (2) the introduction of the functional group is conducted without specifying the introduction position on the molecule A side.
[18] The molecule A-immobilized solid phase support mixture described in [16] above, wherein the introduction of the spacer to the molecule A is conducted via a functional group introduced without specifying the introduction position on the molecule A side.
[19] The molecule A-immobilized solid phase support mixture described in [17] or [18] above, wherein the introduction of the functional group to the molecule A without specifying the introduction position on the molecule A side is based on a chemical reaction or an enzymatic reaction.
[20] The molecule A-immobilized solid phase support mixture described in [19] above, wherein the introduction of the functional group to the molecule A without specifying the introduction position on the molecule A side is based on an enzymatic reaction.
[21] The molecule A-immobilized solid phase support mixture described in [20] above, wherein the enzymatic reaction is conducted using a metabolic enzyme.
[22] The molecule A-immobilized solid phase support mixture described in any one term of [15] to [21] above, which is a solid phase support for affinity chromatography.
[23] A production method for a solid phase support for affinity chromatography comprising binding a molecule A to a solid phase support without specifying the binding position on the molecule A side, and preparing a molecule A-immobilized solid phase support mixture comprising two or more kinds of molecule A-immobilized solid phase supports, wherein said two or more kinds of molecule A-immobilized solid phase supports have the molecule A immobilized thereto at respective different positions on the molecule A.
[24] The production method described in [23] above for a solid phase support for affinity chromatography, wherein the binding of the molecule A to the solid phase support is conducted via a spacer introduced between the molecule A and the solid phase support without specifying the introduction position on the molecule A side.
[25] The production method described in [23] above for a solid phase support for affinity chromatography, wherein (1) the binding of the molecule A to the solid phase support is conducted via a functional group introduced to the molecule A, and (2) the introduction of the functional group is conducted without specifying the introduction position on the molecule A side.
[26] The production method described in [24] above for a solid phase support for affinity chromatography, wherein the introduction of the spacer to the molecule A is conducted via a functional group introduced without specifying the introduction position on the molecule A side.
[27] The production method described in [25] or [26] above for a solid phase support for affinity chromatography, wherein the introduction of the functional group to the molecule A conducted without specifying the introduction position on the molecule A side is based on a chemical reaction or an enzymatic reaction.
[28] The production method described in [27] above for a solid phase support for affinity chromatography, wherein the introduction of the functional group to the molecule A conducted without specifying the introduction position on the molecule A side is based on an enzymatic reaction.
[29] The production method described in [28] above for a solid phase support for affinity chromatography, wherein the enzymatic reaction is conducted using a metabolic enzyme.
[30] A screening method for a molecule B that exhibits a specific interaction with a molecule A, which comprises at least (1) a step of bringing a sample containing or not containing a molecule B into contact with the molecule A-immobilized solid phase support mixture described in any one term of [15] to [22] above, and (2) a step of identifying a molecule that has exhibited or has not exhibited a specific interaction with the molecule A, and selecting the molecule B.

DETAILED DESCRIPTION OF THE INVENTION

Figure 1:
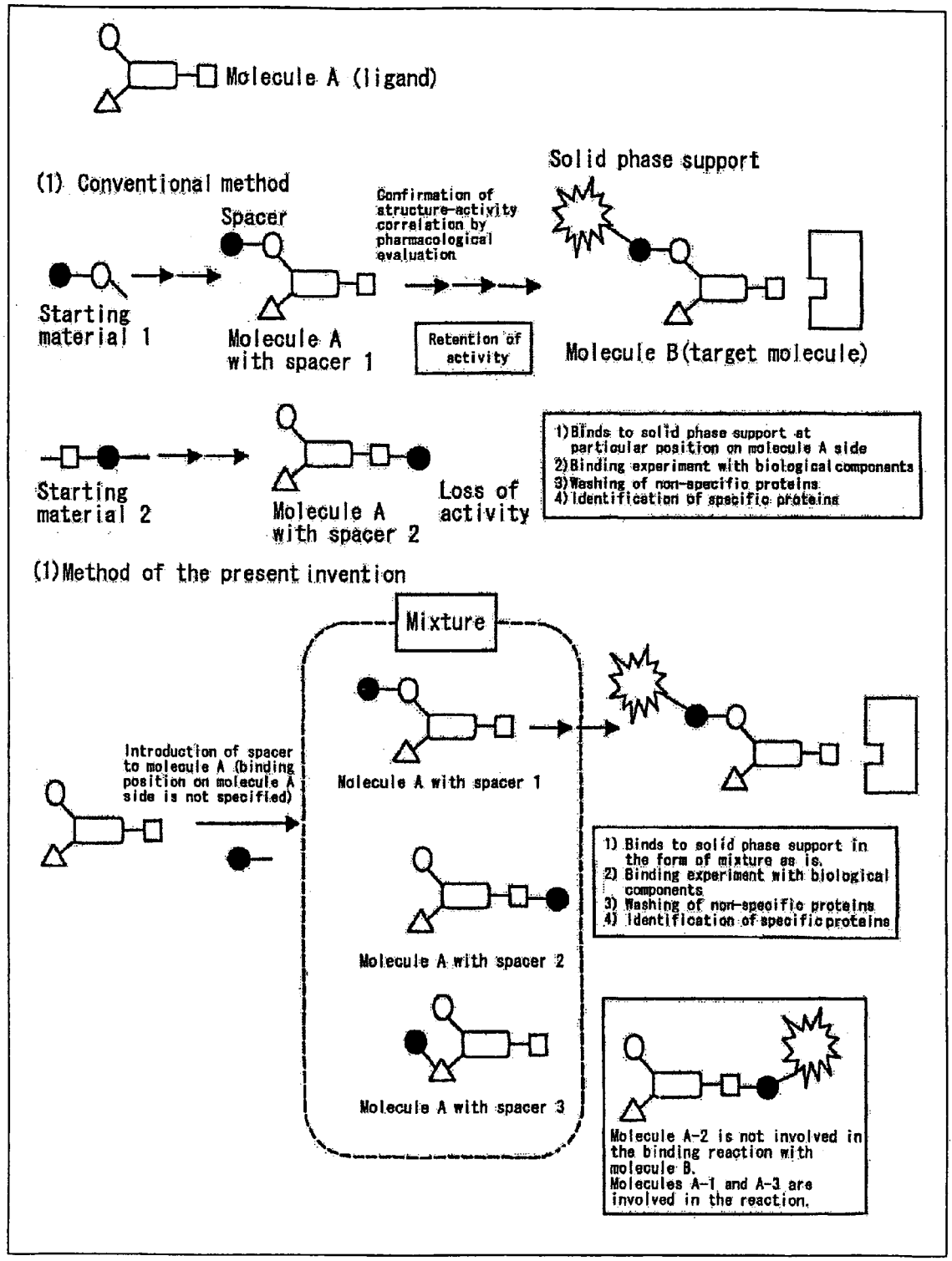
FIG. 1 is a schematic diagram of the concept of the present invention. A comparison with the conventional method is made.

A conceptual diagram of the present invention is shown in FIG. 1. FIG. 1 schematizes a method of preparing a molecule A-immobilized solid phase support by binding a ligand (molecule A: for details see below) to a solid phase support via an appropriate spacer. The conventional method and the method of the present invention are shown. In the conventional method, it is necessary to produce or select only a solid phase support retaining the binding site involved in biological activity on the molecule A side in an intact state with a previous investigation of structure-activity correlation, whereas in the present invention, it is possible to use a solid phase support having the binding site involved in biological activity on the molecule A side damaged, and a solid phase support retaining the binding site in an intact state, in a mixed state, without confirming the binding site to the solid phase support on the molecule A side.

The present invention provides a technology of analyzing the interaction of a molecule to be immobilized to a solid phase support (herein also defined as molecule A, and also referred to as "ligand" for the sake of convenience) and a molecule exhibiting a specific interaction with the former molecule (herein also defined as molecule B, and also referred to as "target molecule" for the sake of convenience), and a technology of identifying and selecting a molecule B on the basis of the analysis. The terms ligand and target molecule as used herein are intended to mean a combination of members that exhibit a specific intermolecular interaction with each other, wherein if one member of the combination is immobilized to a solid phase as a ligand, the other becomes a target molecule; hence, the designations of these members are variable depending on which one to immobilize to the solid phase. The molecule B exhibiting a specific interaction with the molecule A is not limited to one kind, and likewise the molecule A exhibiting a specific interaction with the molecule B is not limited to one kind. The terms molecule A and molecule B as used herein have the symbol A or B given for the sake of convenience to indicate that they are mutually different substances. Each of these terms does not refer to a particular molecule but means each of molecules exhibiting a specific interaction with each other.

A "specific interaction" is a characteristic action to specifically recognize, and bind to, a particular ligand (a particular target molecule) only; the relation of a specific receptor to an agonist or an antagonist, the relation of an enzyme to a substrate, and, for example, the relation of an FK506-binding protein (target molecule) to FK506 (ligand), the relation of a steroid hormone receptor to a steroid hormone (e.g., dexamethasone and glucocorticoid receptor), the relation of HDAC to the anticancer agent trapoxin, and the like apply to a "specific interaction".

In the present invention, "to analyze a specific interaction" is to obtain interaction information on the extent of the specific interaction between a molecule A and a molecule B, which can, for example, be obtained as numerical values of Kd, Ka and the like. In the present invention, "selection" means determining whether or not a molecule exhibits a specific interaction with a molecule A on the basis of the above-described interaction information, and identifying the molecule B.

The solid phase support used in the present invention is not subject to limitation, as long as a specific interaction between a molecule A and a molecule B is produced thereon; one in common use in the art can be used, and is appropriately determined according to the method conducted for the subsequently performed step of identifying and selecting the molecule B. As examples of the material for the solid phase support, resins (polystyrene, methacrylate resin, polyacrylamide and the like), glass, metals (gold, silver, iron, silicon and the like) and the like are used. These solid phases may be of any form, and are appropriately determined according to the kind of the above-described material and the methods conducted for the subsequently performed steps of analyzing the interaction with the molecule B and identifying and selecting the molecule B. For example, plates, beads, thin films, threads, coils and the like can be mentioned; beads composed of a resin simplify the subsequent operation when packed in a column, and metallic thin films can be preferably used as supports for BIACORE and the like based on surface lasmon resonance. It is also preferable to use a glass plate.

Although the solid phase used in the present invention is not subject to limitation as to the material and form thereof, as described above, those showing a structural hindrance such that the molecule A is not immobilizable or the molecule A is immobilizable but unable to exhibit a specific interaction with the molecule B, of course, are undesirable for embodying the present invention because they sometimes complicate the operation due to the necessity of an additional step or do not function well.

In "the method of analyzing the interaction of a molecule A and a molecule B that exhibits a specific interaction with the molecule A" and "the method of selecting a molecule B that exhibits a specific interaction with a molecule A" of the present invention, it is generally premised that a molecule A-immobilized solid phase support mixture containing two or more kinds (or possibly only one kind) of molecule A-immobilized solid phase supports prepared by binding the molecule A to solid phase supports without specifying the binding position on the molecule A side is used. Referring to the two or more kinds of molecule A-immobilized solid phase supports, the molecule A is immobilized to the solid phase supports at respective different positions on the molecule A but the positions are not specified in advance. The binding of the molecule A to the solid phase support is conducted directly or indirectly via a spacer. There are two cases of direct binding: a case where a functional group intrinsic to the molecule A is used, and a case where a functional group newly introduced to the molecule A is used. The new introduction of the functional group is also conducted without specifying the introduction position on the molecule A side. The introduction of the spacer to the molecule A is also conducted without specifying the introduction position on the molecule A side. The distribution of each binding or introduction position is determined dependent on the reactivity of the molecule A to each reagent used for its binding to the solid phase support or for introducing a spacer or functional group to the molecule A. Although the number of binding or introduction positions may be one or more than one, it is sometimes impossible to retain the binding site involved in biological activity on the molecule A side in an intact state with some combinations of the molecule A and the reagent used and/or reaction conditions, because the distribution of each position depends on the reactivity to each reagent and reaction conditions, as described above.

For example, if the mixture does not contain a solid phase support as the means of detecting the molecule B, that is, a solid phase support retaining the binding site involved in biological activity on the molecule A side in an intact state, the mixture possibly consists only of a solid phase support having the binding site involved in biological activity on the molecule A side damaged, as described above, for example; therefore, in such a case, another solid phase support mixture is newly prepared and used with changes in the reagent used and the reaction, and the like. In the method of analyzing the interaction of a molecule A and a molecule B, method of selecting a molecule B, method of screening for a molecule B, and production method for a solid phase support for affinity chromatography, of the present invention, it is preferable to include a step of pre-determining whether or not the mixture includes a solid phase support to be used as a means of detecting the molecule B.

The binding to a solid phase support, the introduction of a spacer, and the introduction of a functional group are conducted without specifying the binding position or introduction position on the molecule A side; it is unnecessary to confirm at which position each step is performed, as long as only a molecule A-immobilized solid phase support having the molecule A immobilized to the solid phase support at a position where the binding to the molecule B is not affected on the molecule A side (functional group and/or spacer introduced if necessary) captures the molecule B, and the molecule B can be isolated and selected or its interaction with the molecule A can be analyzed. As shown in FIG. 1, in the present invention, because any one molecule A-immobilized solid phase support obtained would retain the binding site involved in biological activity on the molecule A side in an intact state, even without specifying the binding position of the molecule A to the solid phase support (on the molecule A side) or the introduction position of the functional group or spacer to the molecule A (on the molecule A side), the binding of the site and the molecule B is assurable. Accordingly, in the present invention, it is possible to detect only the interaction of a molecule A-immobilized solid phase support wherein the molecule A is immobilized to the solid phase support at a position where the binding to the molecule B (target molecule) is not affected, and the molecule B, in a mixture of various molecule A-immobilized solid phase supports (may further contain a raw material and a decomposition product), without being concerned about the structure-activity correlation of the molecule A.

Although the terms "binding position on the molecule A side" and "introduction position on the molecule A side" as used herein are used distinguishably depending on the other member bound or introduced to the molecule A, they have the same meaning in that both members (molecule A and solid phase support, molecule A and spacer, molecule A and functional group) are joined together without specifying the position involved in the reaction on the molecule A side.

Furthermore, the above-described molecule A-immobilized solid phase support mixture used in "the method of analyzing the interaction of a molecule A and a molecule B that exhibits a specific interaction with the molecule A" and "the method of selecting a molecule B that exhibits a specific interaction with a molecule A" is useful as a solid phase support for affinity chromatography. Accordingly, the present invention provides a production method for a solid phase support for affinity chromatography comprising binding a molecule A to a solid phase support to immobilize the molecule A without specifying the binding position on the molecule A side, and preparing a molecule A-immobilized solid phase support mixture comprising two or more kinds of molecule A-immobilized solid phase supports, wherein the two or more kinds of molecule A-immobilized solid phase supports have the molecule A immobilized thereto at respective different positions on the molecule A. Despite its identity as a molecule A-immobilized solid phase support mixture comprising two or more kinds of molecule A-immobilized solid phase supports, the solid phase support for affinity chromatography obtained by this method can fully exhibit affinity for the molecule B and can be used to select the molecule B or to analyze an interaction with the molecule B, without the need of further purification or fractionation.

The molecule A-immobilized solid phase support mixture obtained is specifically exemplified by the modes shown below.

1) In Case Where a Functional Group Intrinsic to Molecule A is Used

In a case where a functional group intrinsic to the molecule A (ligand) is used directly for the binding to the solid phase support, a target molecule for the ligand is searched by using the functional group directly in the immobilization reaction, or indirectly in the immobilization reaction via an appropriate spacer.

In a case where the functional group of the ligand is subjected directly to the immobilization reaction, the ligand and the solid phase support are reacted under conditions suitable for the immobilization.

Specifically, by dissolving the ligand in an aqueous or organic solvent or a mixed solvent thereof, and mixing the thus-obtained ligand solution and the solid phase (solid phase is also preferably suspended in an aqueous or organic solvent or a mixed solvent thereof in advance), or by subjecting the ligand and the solid phase support to a reaction to form a covalent bond or a non-covalent bond, such as an amide bond, a Schiff base bond, a C—C bond, an ester bond, a hydrogen bond or a hydrophobic interaction, the ligand is immobilized to the solid phase. The aqueous or organic solvents for dissolving or suspending the ligand and the solid phase may be identical or not; for example, an aqueous solvent such as water or a buffer solution, and an organic solvent such as an alcohol (methanol, ethanol, and the like), dimethylformamide, dichloromethane or acetonitrile, can be mentioned. A mixed solvent thereof can also be used preferably. The reaction used to immobilize the ligand to the solid phase is chosen according to the kind of the functional group on the ligand to be immobilized and the like, and the ligand is immobilized to the solid phase using an appropriately chosen known technique.

Temperatures during the series of reactions and treatments are not subject to limitation, as long as they are suitable for the immobilization reaction chosen and the ligand remains stable; the reactions are normally carried out at 0° C. to 100° C., preferably at room temperature to 70° C. Time of mixing the solid phase and the ligand is also not subject to limitation, as long as the ligand is immobilized to the solid phase; this mixing time is appropriately set according to the immobilization reaction chosen, the ligand to be immobilized, the kind of solid phase used, and the like. Reaction time is normally 1 hour to several days, preferably 2 hours to overnight. In the binding reaction, the amount of the ligand appropriately chosen according to the immobilization reaction used is generally in excess of that of the solid phase, but not all bindable sites on the solid phase or of the ligand need to be subjected to the reaction; the ligand need not always be in excess because the object of the present invention can be accomplished even if the ligand is partially immobilized to the solid phase.

The reaction used to immobilize the ligand to the solid phase support by forming an amide bond, a Schiff base, a C—C bond, an ester bond, a hydrogen bond, a hydrophobic interaction or the like, is a technique known in the art, and can be carried out in accordance with conventional methods in terms of reaction reagents, reaction conditions and the like, which may be changed as appropriate if necessary.

In a case where a functional group intrinsic to the ligand is used in the immobilization reaction via an appropriate spacer, the spacer is first introduced to the functional group intrinsic to the ligand. The introduction of the spacer is also conducted without specifying the introduction position on the molecule A side, and can generally be conducted using a known method available to introduce a spacer to a compound. Because the mixture can be used without the need of specifying the spacer introduction position in the present invention, the ligand and the spacer are reacted under conditions suitable for introduction of the spacer, without considering the structure-activity correlation.

Specifically, the ligand is dissolved in an aqueous or organic solvent or a mixed solvent thereof, the ligand solution obtained and the spacer (spacer is also preferably dissolved in an aqueous or organic solvent or a mixed solvent thereof in advance) are mixed, and the spacer and the ligand are bound using a method known in the art selected according to the functional group of the ligand to be immobilized. The spacer may be derivatized to confer reactivity if necessary. For example, in the case of a ligand having a hydroxyl group as the functional group, the spacer is preferably introduced to the ligand by carrying out a dehydration reaction in the presence of a dehydrating agent using a carboxylic acid or a derivative thereof as the spacer. As the aqueous or organic solvent used here, the same as above is used.

Temperatures during the series of reactions and treatments are not subject to limitation, as long as the reaction proceeds and the ligand and spacer remain stable; the reactions and treatments are normally carried out at 0° C. to 100° C., preferably at room temperature to 70° C. Reaction time is also not subject to limitation, and is appropriately set according to the chemical reaction carried out, the kinds of ligand and spacer used, and the like. Reaction time is normally 1 hour to several days, preferably 2 hours to overnight. In the binding reaction, the amount of the spacer used is generally in excess of that of the ligand, but not all bindable sites on the ligand or on the spacer need to be subjected to the reaction; the spacer need not always be in excess amount because the object of the present invention can be accomplished even if the spacer is partially introduced to the ligand.

A "spacer" refers to a substance that is introduced to become a group that interlies between the solid phase support and the ligand at the time of immobilization of the ligand to the solid phase support; here, "a spacer interlies" means that the spacer is present between a functional group in the solid phase and a functional group in the ligand. The spacer binds to the functional group in the solid phase at one end and binds to the functional group in the ligand at the other end. A spacer in common use in the art for immobilization of a ligand to a solid phase can be used (also referred to as spacer or linker); the spacer may be a newly synthesized one, as long as it is capable of functioning as a group presented between the solid phase support and the ligand. The binding of the spacer and the ligand is based on a covalent bond or a non-covalent bond, such as an amide bond, a Schiff base, a C—C bond, an ester bond, a hydrogen bond or a hydrophobic interaction.

After a spacer is introduced, a ligand incorporating the spacer is bound to the solid phase support without specifying the binding position on the molecule A side in the same manner as the method performed in the above-described "case where the functional group of the ligand is subjected directly to the immobilization reaction".

2) In Case Where No Available Functional Group is Present in the Ligand

After a chemical or enzymatic reaction is carried out to add a functional group to the ligand, a target molecule for the ligand is searched by using the functional group in the immobilization reaction, or via an appropriate spacer in the immobilization reaction (see 1 above).

The addition of the functional group is also conducted without specifying the introduction position on the molecule A side.

As the method of chemically adding a functional group, nitration, halogenation and various subsequent reactions and the like can be mentioned. For example, an amino group can be added by carrying out a reduction reaction after nitration, and can be converted to various substituents (amide, N-alkyl, sulfonamide, and the like). Also, a carboxyl group, ester group, aryl group and the like can be added by carrying out an oxidative addition reaction after halogenation.

As examples of the method of adding a functional group using an enzymatic reaction, methods using a metabolic enzyme such as an oxidase, reductase or hydrolase, particularly a drug-metabolizing enzyme (S-9 Mix and the like), can be mentioned. The enzyme used is not subject to limitation as to derivation, may be derived from a microorganism such as a bacterium (genus *Pseudomonas* and the like), actinomycete (genus *Streptomyces* and the like) or fungus (genus *Aspergillus* and the like) or from a mammalian cell or tissue, and may be derived from a transformant prepared by gene recombination technology so that such a metabolic enzyme is expressed. Because of the advantage of availability in large amounts, an enzyme derived from a microorganism or transformant is preferred.

For example, a supernatant obtained by centrifuging a liver tissue cell homogenate at 9,000×g (S-9 fraction: commercially available as S-9 Mix) is used. It is known that various functional groups are introduced to the ligand by carrying out a reaction of this enzyme and the ligand. For example, introduction of a hydroxyl group by aromatic ring or alkyl chain hydroxylation, introduction of an epoxy group by double bond epoxidation, production of an amino group resulting from N-alkylamino group dealkylation, production of a carbonyl group by oxidative deamination, production of a carboxyl group, amino group or hydroxyl group by ester or amide bond hydrolysis, and the like are known (Shinpan Yakubutsu Taisha (Introduction to Drug Metabolism, New Edition), written by G. G. Gibson et al., translated under supervision of Toshiro Murata, Kodansha, ISBN 4-06-139775-3).

Furthermore, the functional group may be activated in advance of the binding to the solid phase support or the binding to the spacer. Specifically, various kinds of functional groups (for example, hydroxyl group, amino group, carboxyl group and the like) can be activated with a highly reactive reagent, for example, phosgene.

Whether or not the molecule A has been immobilized to the solid phase support can be confirmed by using a color developing reaction based on a particular structure or substituent and the like contained in the molecule A or a spacer or functional group that has been bound and introduced to the molecule A in advance, and the like. For example, the ninhydrin reaction, which recognizes an amino group, and the like can be used.

In the present invention, the molecule A (ligand) to be immobilized to a solid phase support is not subject to limitation, and may be a known compound or a novel compound that will be developed in the future. Also, the molecule A (ligand) may be a low-molecular compound or a high-molecular compound. Here, a low-molecular compound refers to a compound having a molecular weight of about less than 1000; for example, an organic compound commonly usable as a pharmaceutical, a derivative thereof, and an inorganic compound can be mentioned; specifically, a compound produced by making use of a method of organic synthesis and the like, a derivative thereof, a naturally occurring compound, a derivative thereof, a small nucleic acid molecule such as a promoter, various metals, and the like can be mentioned; and desirably, an organic compound usable as a pharmaceutical, a derivative thereof, and a nucleic acid molecule can be referred to. Also, as the high-molecular compound, a compound having a molecular weight of about 1000 or more, which is a protein, a polynucleic acid or a polysaccharide, and a combination thereof, and the like can be mentioned. These low-molecular compounds or high-molecular compounds are commercially available if they are known compounds, or can be prepared via steps such as of collection, production and purification according to various publications. These may be of natural origin, or may be prepared by gene engineering, or may be obtained by semi-synthesis and the like.

In the present invention, a process of selecting a molecule B on the basis of the specific interaction with the above-described molecule A on a solid phase having the molecule A immobilized thereon is necessary. Therefore, the molecule B is not subject to limitation, as long as it specifically interacts with the molecule A, and is expected to be a known compound in some cases or a novel substance in other cases. The molecule B may be a low-molecular compound or a high-molecular compound. When the molecule B is a low-molecular compound, the molecule B can be selected on the basis of the specific interaction of low-molecular compound and low-molecular compound with the molecule A that is a low-molecular compound, or on the basis of the specific interaction of high-molecular compound and low-molecular compound with the molecule A that is a high-molecular compound. Also, when the molecule B is a high-molecular compound, the molecule B can be selected on the basis of the specific interaction of low-molecular compound and high-molecular compound with the molecule A that is a low-molecular compound, or on the basis of the specific interaction of high-molecular compound and high-molecular compound with the molecule A that is a high-molecular compound. A preferable combination of the molecule A and the molecule B is the combination of a low-molecular compound and a high-molecular compound, or the combination of a high-molecular compound and a high-molecular compound.

Analysis of the interaction with the molecule B and selection of the molecule B are conveniently conducted on the solid phase. When a candidate substance is anticipated as the molecule B, it is possible to bring the candidate substance alone into contact with the molecule A immobilized on the solid phase, measure the interaction therebetween, and determine whether or not the candidate substance is the molecule B, that is, whether or not the candidate substance is a target molecule for the molecule A; usually, by bringing a sample containing a plurality of substances (high-molecular compounds and/or low-molecular compounds) into contact with the molecule A, and determining the presence or absence of an interaction of each of the plurality of substances (high-molecular compounds and/or low-molecular compounds) and the molecule A, and the extent of the interaction, whether or not the candidate substance is the molecule B is determined for selection. Here, the sample containing a plurality of substances may consist essentially of known compounds, may contain some novel compounds, and may consist essentially of novel compounds. However, from the viewpoint of search of target molecules for ligands, or the recent advances in proteome analysis, it is desirable that the sample be a mixture essentially of compounds of known structures. As the sample consisting essentially of known compounds, a mixture of purified proteins prepared by gene engineering using *Escherichia coli* and the like, and the like can be mentioned; as the sample containing some novel compounds, a cell or tissue extract (lysate) can be mentioned; as the sample that consists essentially of novel compounds, a mixture of novel proteins whose functions and structures are yet unknown, or newly synthesized compounds and the like, can be mentioned. When the sample is a mixture, especially containing known compounds, the contents of these compounds in the sample may optionally be set at desired levels in advance. From the viewpoint of search of target molecules for ligands, the molecule B to be selected is preferably a low-molecular compound or a high-molecular compound, and for search of a target molecule in the body of an animal such as a human, the molecule B is preferably a high-molecular compound.

It is particularly preferable that the sample already have biological activity on the ligand; the sample used is changed appropriately depending on the ligand to be immobilized, and the best suited one is chosen. The choice of the sample is preferably conducted before performing the method of analyzing the interaction of a molecule A and a molecule B, method of selecting a molecule B, method of screening for a molecule B, and a production method for a solid phase support for affinity chromatography, of the present invention.

The present invention provides a method of screening for a molecule B that exhibits a specific interaction with a molecule A using the molecule A immobilized on the above-described solid phase. The screening method comprises at least the following steps.

(1) Step of bringing a sample containing or not containing a molecule B into contact with the above-described molecule A-immobilized solid phase support mixture.

The sample used in this step contains a plurality of substances as described above. The mode of embodiment thereof is not subject to limitation, and can be changed appropriately according to the solid phase support used and what principles, means and methods to use for the subsequent steps. For example, when using a column packed with a bead resin with the molecule A immobilized thereon, the sample is preferably liquid. In the case of a sample not containing the molecule B, identification and analysis of a molecule (a plurality of kinds present in some cases) that has not exhibited a specific interaction with the molecule A are conducted in step (2). In the case of a sample containing the molecule B, the molecule B (a plurality of kinds present in some cases) that has exhibited a specific interaction with the molecule A is identified and analyzed in step (2). The method of bringing the sample and the solid phase support into contact with each other is not subject to limitation, as long as the molecule B in the sample can bind to the molecule A immobilized to the solid phase support, and can be changed appropriately according to the solid phase support used and what principles, means and methods to use for the identification or analysis in the subsequent steps. For example, when using a column packed with a bead resin with the molecule A immobilized thereon, this method is conveniently performed by adding the liquefied sample to the column, and passing it through the column.

(2) Screening method for a molecule B that exhibits a specific interaction with a molecule A, which comprises a step of identifying a molecule that has exhibited or has not exhibited a specific interaction with the molecule A, and selecting the molecule B.

Although this step can be changed appropriately according to the solid phase support used, the kind of the molecule A immobilized, and the like, it is conducted by various methods in common use in the art to identify a low-molecular compound or a high-molecular compound. The step will also be performed by a method that will be developed in the future. For example, when using a column packed with a molecule A-immobilized bead resin as the molecule A-immobilized solid phase support, the molecule B is bound to the molecule A by the subsequent addition of the sample. It is also possible to dissociate the bound molecule B from the molecule A by a treatment such as altering the polarity of the buffer solution or further adding the molecule A in excess, and then identify the molecule B, or to extract the molecule B with a surfactant and the like while it remains bound to the molecule A on the solid phase, and then identify the molecule B. As the method of identification, specifically, known techniques such as electrophoresis, immunoblotting and immunoprecipitation, which employ an immunological reaction, chromatography, mass spectrometry, amino acid sequencing, and NMR (especially for low-molecules), or combinations of these methods can be used. Although the step of identifying a molecule that does not bind to the molecule A can also be conducted in accordance with the above-described method of identifying a molecule that binds to the molecule A, it is preferable that a treatment such as concentration or crude purification be conducted in advance before entering the identification step, since a molecule contained in the column effluent is the subject of identification. On the basis of the data obtained and reported information, each molecule is identified, and whether or not it is a target molecule for the molecule A is determined.

Also, this step may be automated. For example, it is also possible to directly read data on various molecules obtained by two-dimensional electrophoresis, and identify the molecules on the basis of existing databases.

Whether or not this binding is specific can be confirmed by conducting an antagonism test. Specifically, the following method can be mentioned. First, a sample containing a molecule judged to be a target molecule is mixed with a free molecule A and fully reacted. Subsequently, the mixed solution obtained is brought into contact with a molecule A-immobilized solid phase support mixture. The kind of molecule trapped by the solid phase support is compared from a case (control) where the sample was not mixed with the free molecule A. If the molecule previously judged to be a target molecule is really the target molecule, the molecule B band observed in the control should have disappeared or attenuated.

EXAMPLES

The present invention is hereinafter described in more detail by means of the following Production Examples, Examples and Experimental Examples, which Examples and Experimental Examples, however, are not to be construed as limiting the scope of the present invention. Note that the abbreviations in the individual structural formulas are as follows.
Me: Methyl group
TBDPS: t-Butyldiphenylsilyl group
TBS: t-Butyldimethylsilyl group Example 1

Introduction of Spacer to FK-506 (Position not Specified)

Synthesis of 17-allyl-1,14-di-hydroxy-12-{2-[4-(7-carboxy-heptanoyl-oxy)-3-methoxy-cyclohexyl]-1-methyl-vinyl}-23,25-dimethoxy-13,19,21,27-tetramethyl-11,28-dioxa-4-aza-tricyclo[22.3.1.0$^{4,9}$]octacos-18-ene-2,3,10,16-tetraone (mixture A)

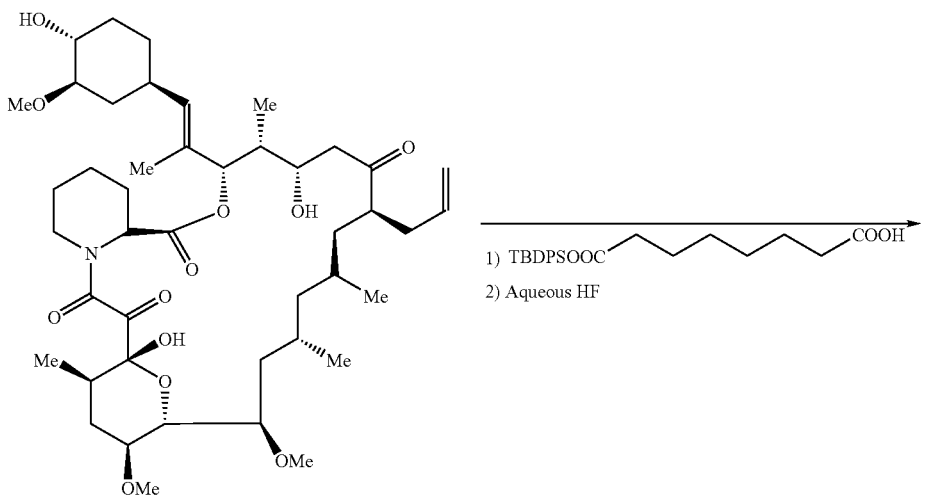

1(FK506)

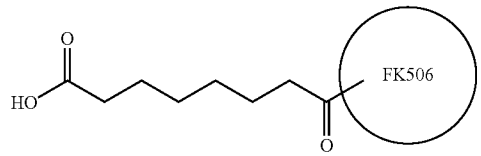

Mixture A 17-allyl-1,14-di-hydroxy-12-[2-(4-hydroxy-3-methoxy-cyclohexyl)-1-methyl-vinyl]-23,25-dimethoxy-13,19,21,27-tetramethyl-11,28-dioxa-4-aza-tricyclo[22.3.1.0$^{4,9}$] octacos-18-ene-2,3,10,16-tetraone (FK-506, 1, 3.3 mg, 4.10 μmol) was twice boiled together with benzene, and dissolved in dichloromethane (39 μl), and 16.2 μl (4.09 μmol) of a solution of O-mono(tert-butyl-diphenyl-silanyl)octanedioic acid in dichloromethane (100 mg/ml) was added. After this was dissolved by the addition of 1-[3-(dimethylamino)propyl]-3-ethylcarbodiimide hydrochloride (WSC/HCl, 0.94 mg, 4.90 μmol) and 23 μl (1.88 μmol) of a solution of 4-dimethylaminopyridine in dichloromethane (10 mg/ml) at room temperature, the solution was allowed to stand for 1.5 hours. This solution was extracted by the addition of dichloromethane (150 μl) and saturated aqueous sodium carbonate (150 μl). The organic phase collected was concentrated by blowing a nitrogen stream. After the syrup obtained was dissolved by the addition of acetonitrile (28 μl), 46-48% aqueous hydrogen fluoride (6.5 μl) was added at room temperature, and the solution was allowed to stand for 1.5 hours. This solution was extracted by the addition of ethyl acetate (100 μl) and saturated aqueous sodium carbonate (100 μl), and the organic phase was concentrated by blowing a nitrogen stream, to yield a syrup of mixture A. The mixture A was used as is without purification and the like in the next step. The mixture A was used while no structural information was available about whether or not the mixture A contains a compound having the spacer introduced thereto only at a position where the binding to FKBP12 is not affected, for example, 17-allyl-1,14-di-hydroxy-12-{2-[4-(7-carboxy-heptanoyl-oxy)-3-methoxy-cyclohexyl]-1-methyl-vinyl}-23,25-dimethoxy-13,19,21,27-tetramethyl-11,28-dioxa-4-aza-tricyclo[22.3.1.0$^{4,9}$] octacos-18-ene-2,3,10,16-tetraone shown in Reference Production Example 2, or contains FK506 having the spacer introduced therein at a position where there is a contribution to the binding to FKBP12, or contains FK506 having a plurality of spacers introduced thereto, and the like.

Example 2

Immobilization of Mixture of FK-506 with Spacer to TOYO-Pearl Resin

The syrup obtained in Example 1 was centrifuged with benzene and concentrated under reduced pressure, and dissolved in a mixed solvent of methylene chloride/N-methyl-2-pyrrolidone (4/1) (0.3 ml), and WSC (1.44 mg, 7.5 μmol) and 1-hydroxybenzotriazole (1.01 mg, 7.5 μmol) were added. This solution was added to 10 μl of TOYO-Pearl resin (TSK-gel AF-amino; 0.01 mmol amine is present in 100 μl) and shaken at room temperature overnight. After completion of the reaction, the resin was thoroughly washed with a mixed solvent of methylene chloride/N-methyl-2-pyrrolidone (4/1), and DMF, and the percent condensation yield was determined by the ninhydrin test (about 29%). A mixed solution of acetic anhydride/DMF (1/4) (0.3 ml) was added to the resin obtained, and this was followed by shaking at room temperature for 30 minutes. After completion of the reaction, the resin was thoroughly washed with methylene chloride, dimethylformamide (DMF) and 20% aqueous ethanol, and this resin was used as the affinity resin in the subsequent experiments.

Reference Production Example 1

Synthesis of 17-allyl-14-(tert-butyl-dimethyl-silanyloxy)-1-hydroxy-12-{2-[4-(7-(tert-butyl-dimethyl-silanyloxy-carbonyl)heptanoyl-oxy)-3-methoxy-cyclohexyl]-1-methyl-vinyl}-23,25-dimethoxy-13,19,21,27-tetramethyl-11,28-dioxa-4-aza-tricyclo[22.3.1.0$^{4,9}$]octacos-18-ene-2,3,10,16-tetraone

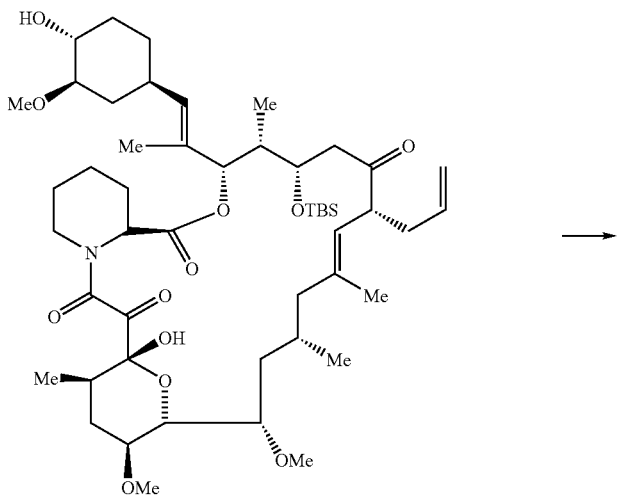

-continued

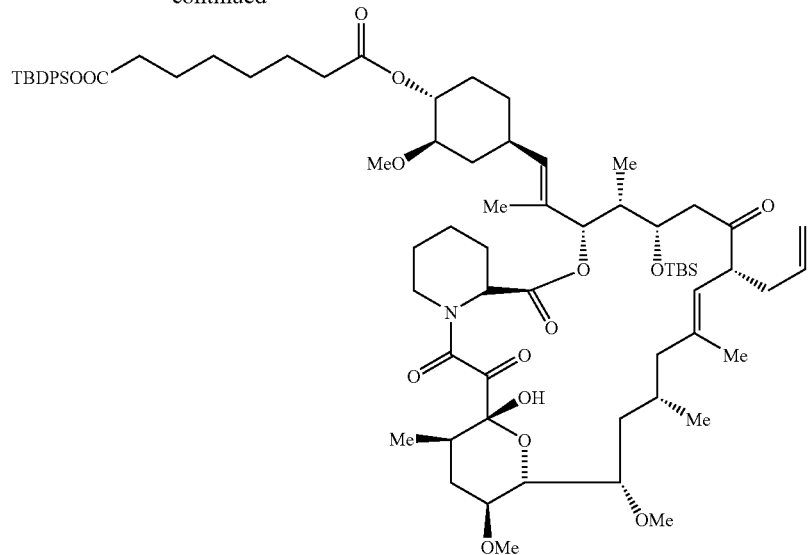

A mixture of 17-allyl-14-(tert-butyl-dimethyl-silanyloxy)-1-hydroxy-12-[2-(4-hydroxy-3-methoxy-cyclohexyl)-1-methyl-vinyl]-23,25-dimethoxy-13,19,21,27-tetramethyl-11,28-dioxa-4-aza-tricyclo[22.3.1.0$^{4,9}$]octacos-18-ene-2,3,10,16-tetraone (138 mg, 0.15 mmol), O-mono(tert-butyl-dimethyl-silanyl)octanedioic acid (86.7 mg, 0.218 mmol), dimethylaminopyridine (DMAP; 16.5 mg, 0.098 mmol), 1-[3-(dimethylamino)propyl]-3-ethylcarbodiimide hydrochloride (EDC/HCl; 69.1 mg, 0.261 mmol) and methylene chloride (CH$_2$Cl$_2$; 1 ml) was stirred at room temperature for 1.5 hours. The reaction product was poured over an ethyl acetate-water mixed solution and extracted. The organic phase obtained was washed with water and saline, and dried over magnesium sulfate (MgSO$_4$). After the MgSO$_4$ was separated by filtration, the filtrate was concentrated under reduced pressure. The residue thus obtained was purified using a silica gel column (eluted with 20% AcOEt (in n-hexane)) to yield the desired 17-allyl-14-(tert-butyl-dimethyl-silanyloxy)-1-hydroxy-12-{2-[4-(7-(tert-butyl-dimethyl-silanyloxy-carbonyl)heptanoyl-oxy)-3-methoxy-cyclohexyl]-1-methyl-vinyl}-23,25-dimethoxy-13,19,21,27-tetramethyl-11,28-dioxa-4-aza-tricyclo[22.3.1.0$^{4,9}$] octacos-18-ene-2,3,10,16-tetraone (44 mg, 24.6%).

$^1$H-NMR (CDCl$_3$)δ: −0.1-0.1 (12H,m), 0.7-2.6 (47H,m), 0.85 and 0.86 (18H,s), 1.50 (3H,s), 1.63 (3H,s), 2.75 (1H,m), 3.31 (3H,s), 3.35 (3H,s), 3.39 (3H,s), 4.05 (1H,m), 3.0-4.4 (6H), 4.5-5.8 (9H,m).

Reference Production Example 2

Synthesis of 17-allyl-1,14-di-hydroxy-12-{2-[4-(7-carboxy-heptanoyl-oxy)-3-methoxy-cyclohexyl]-1-methyl-vinyl}-23,25-dimethoxy-13,19,21,27-tetramethyl-11,28-dioxa-4-aza-tricyclo[22.3.1.0$^{4,9}$]octacos-18-ene-2,3,10,16-tetraone

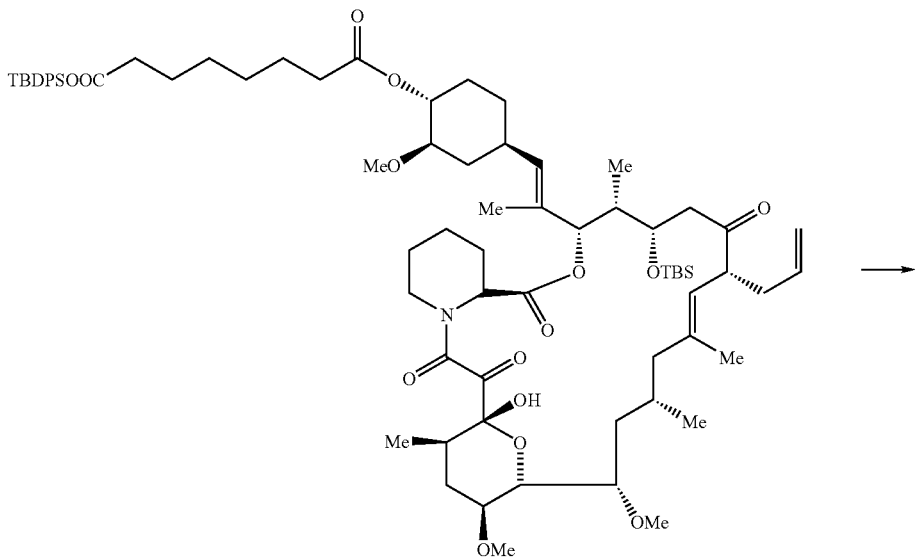

-continued

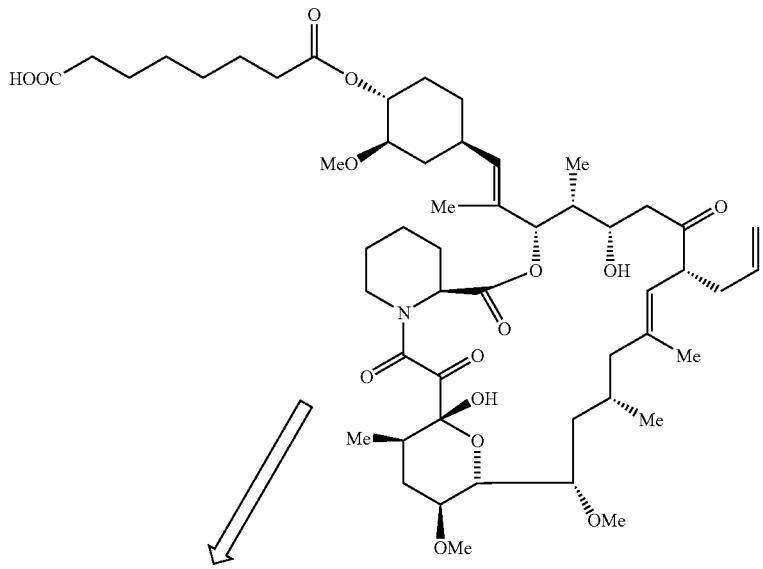

Hereinafter abbreviated as follows:

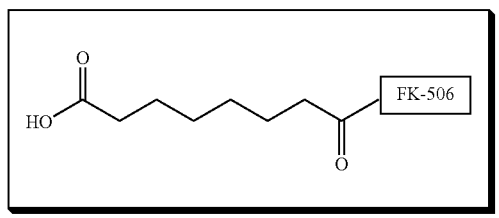

To a mixture of the 17-allyl-14-(tert-butyl-dimethyl-silanyloxy)-1-hydroxy-12-{2-[4-(7-(tert-butyl-dimethyl-silanyloxy-carbonyl)heptanoyl-oxy)-3-methoxy-cyclohexyl]-1-methyl-vinyl}-23,25-dimethoxy-13,19,21,27-tetramethyl-11,28-dioxa-4-aza-tricyclo[22.3.1.0$^{4,9}$]octacos-18-ene-2,3,10,16-tetraone prepared in Reference Production Example 1 (44 mg, 0.037 mmol) and acetonitrile (0.88 ml), 46-48% aqueous hydrogen fluoride (HF) (0.12 ml) was gently added, and this was followed by overnight stirring at room temperature. The reaction product was poured over an ethyl acetate-water mixed solution and extracted. The organic phase obtained was washed with water and saline, and dried over magnesium sulfate (MgSO$_4$). After the MgSO$_4$ was separated by filtration, the filtrate was concentrated under reduced pressure. The residue thus obtained was purified using a silica gel column (5% methanol (in chloroform)) to yield the desired 17-allyl-1,14-di-hydroxy-12-{2-[4-(7-carboxy-heptanoyl-oxy)-3-methoxy-cyclohexyl]-1-methyl-vinyl}-23,25-dimethoxy-13,19,21,27-tetramethyl-11,28-dioxa-4-aza-tricyclo[22.3.1.0$^{4,9}$]octacos-18-ene-2,3,10,16-tetraone (14.2 mg, 40%).

$^1$H-NMR (CDCl$_3$)δ: 0.7-2.6 (47H,m), 1.50 (3H,s), 1.63 (3H,s), 2.75 (1H,m), 3.31 (3H,s), 3.35 (3H,s), 3.39 (3H,s), 4.05 (1H,m), 3.0-4.4 (6H), 4.5-5.8 (11H,m).

MS (m/z): 960 (M+)

Reference Production Example 3

Synthesis of TOYO-Pearl Resin (TSKgel AF-amino) with FK506

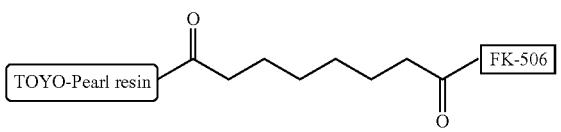

A mixture of the 17-allyl-1,14-dihydroxy-12-{2-[4-(7-carboxy-heptanoyl-oxy)-3-methoxy-cyclohexyl]-1-methyl-vinyl}-23,25-dimethoxy-13,19,21,27-tetramethyl-11,28-dioxa-4-aza-tricyclo[22.3.1.0$^{4,9}$] octacos-18-ene-2,3,10,16-tetraone prepared in Reference Production Example 2 (38.4 mg, 0.04 mmol), TOYO-Pearl resin (TSKgel AF-amino, 100 µl, free amino group (available amino group) 0.01 mmol), EDC/HCl (9.2 mg, 0.048 mol), 1-hydroxybenzotriazole (HOBt; 6.5 mg, 0.048 mmol) and DMF (1 ml) was stirred at room temperature for 6 hours. The reaction end point was confirmed as the time when no residual amino group became visually observable by the ninhydrin reaction. The reaction rate at this time was calculated to be about 82%. After confirmation of completion of the reaction, the resin was washed with DMF five times. Acetic anhydride (100 µl) and DMF (400 µl) were added thereto, and this was followed by stirring at room temperature for 1 hour. Subsequently, the resin was thoroughly washed with DMF, and the TOYO-Pearl resin with FK506 obtained was used as the control affinity resin in the binding experiments described below.

Example 3

Direct Immobilization of FK506 to TOYO-Pearl Resin

FK-506 (3.3 mg, 4.1 µmol) was centrifuged with benzene and concentrated under reduced pressure, and dissolved in DMF (0.6 ml), and WSC (1.00 mg, 5.2 µmol) and 1-hydroxybenzotriazole (0.7 mg, 5.2 µmol) were added. This solution was added to 10 µl of TOYO-Pearl resin (TSKgel AF-amino; 0.01 mmol amine is present in 100 µl), and this was followed by overnight shaking at room temperature. After completion of the reaction, the resin was thoroughly washed with DMF. A mixed solution of acetic anhydride/DMF (1/4) (0.3 ml) was added to the resin obtained, and this was followed by shaking at room temperature for 30 minutes. After completion of the reaction, the resin was thoroughly washed with DMF and 20% aqueous ethanol to yield an FK506-bound affinity resin.

Example 4

Binding Experiment 1

(1) Preparation of Lysate

The rat brain (2.2 g) was mixed in a mixed solution A (0.25M sucrose, 25 mM Tris buffer (pH 7.4), 22 ml) and prepared as a homogenate, which was then centrifuged at 9500 rpm for 10 minutes. The centrifugal supernatant was collected and further centrifuged at 50000 rpm for 30 minutes. The supernatant thus obtained was used as the lysate. Note that the experiment was conducted at 4° C. or on ice throughout the entire time course.

(2) Binding Experiment

A lysate binding experiment was conducted per the following procedures using the FK506-bound affinity resin prepared in Example 2 and the conventional FK506-bound affinity resin prepared in Reference Production Example 3, which had proven to be effective. Note that the lysate was used after being diluted with the mixed solution 1 at a dilution rate of 1/2. Ten microliters of each of the various FK506-bound affinity resins was used.

Each FK506-bound affinity resin and the lysate (1 ml) were gently shaken at 4° C. overnight. Thereafter, the supernatant was removed, and the remaining FK506-bound affinity resin was thoroughly washed with the mixed solution 1 four times to thoroughly clean the surface of the FK506-bound affinity resin.

Figure 2:
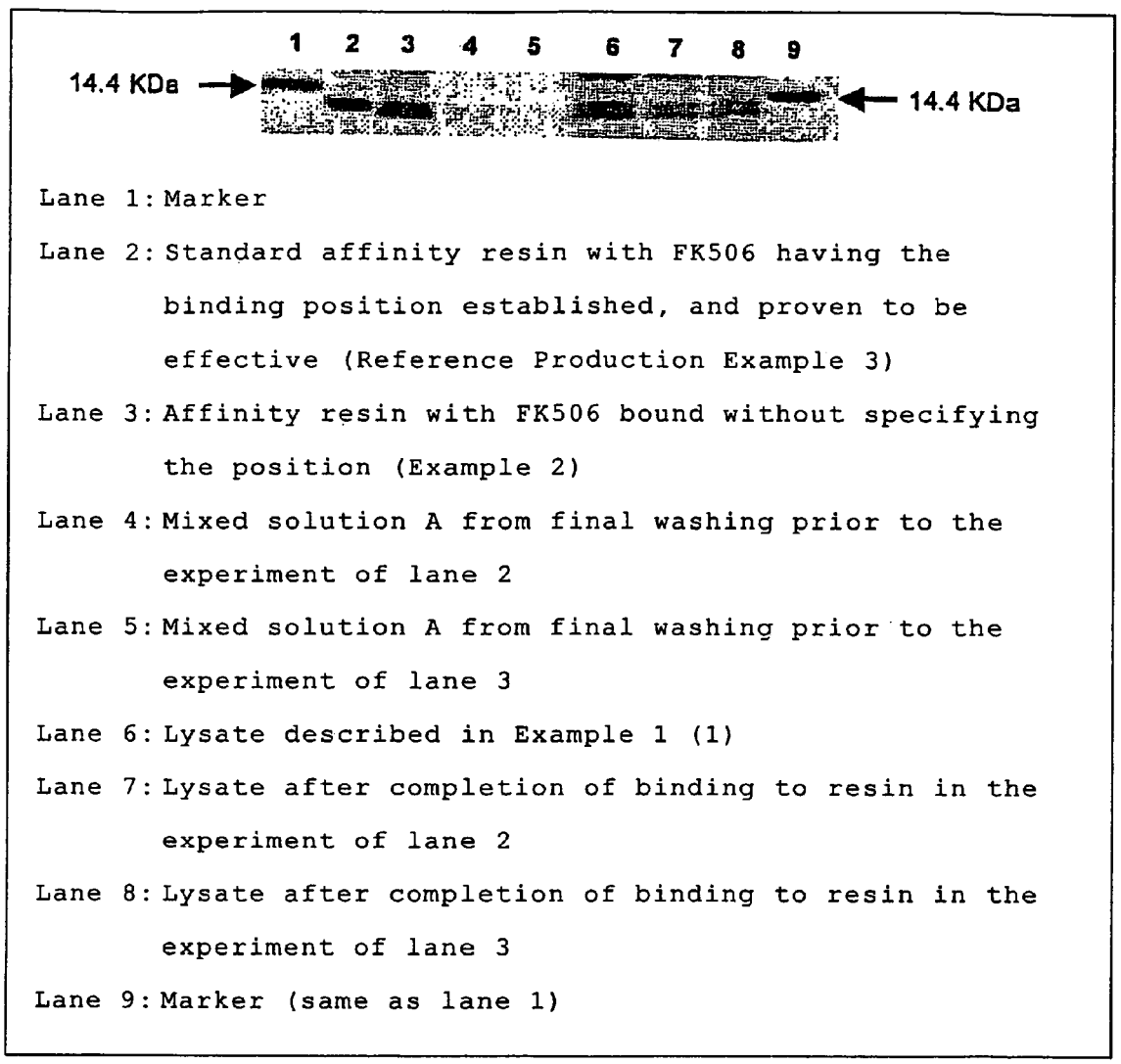
FIG. 2 is an electrophoretogram showing the results of detection of an FK506-binding protein (FKBP12) in a lysate using an FK506-bound affinity resin of the present invention (Example 2).
Lane 1: Marker
Lane 2: Standard affinity resin with FK506 having the binding position established, and proven to be effective (Reference Production Example 3)
Lane 3: Affinity resin with FK506 bound without specifying the position (Example 2)
Lane 4: Mixed solution A from final washing prior to the experiment of lane 2
Lane 5: Mixed solution A from final washing prior to the experiment of lane 3
Lane 6: Lysate described in Example 1 (1)
Lane 7: Lysate after completion of binding to resin in the experiment of lane 2
Lane 8: Lysate after completion of binding to resin in the experiment of lane 3
Lane 9: Marker (same as lane 1)

To the FK506-bound affinity resin thus obtained, 20 µl of a loading buffer for SDS (nacalai cat. NO=30566-22, sample buffer solution with 2-ME (2-mercaptoethanol) for electrophoresis, (2×) for SDS PAGE) was added; this was followed by heating at 25° C. for 10 minutes. The sample solution thus obtained was separated using a commercially available SDS gel (BioRad readyGel J, 15% SDS, cat. NO=161-J341), and the SDS gel was analyzed. For comparison, the affinity resin shown in Reference Production Example 3, which retains FK506 having a spacer selectively bound thereto at a known position where the binding to FKBP12 is not affected was used (FIG. 2). The affinity resin shown in Reference Production Example 3 has been confirmed as binding to FKBP12 efficiently (Japanese Patent Application No. 2002-222226).

Results focusing on the binding to FKBP12 are shown in FIG. 2.

As seen from FIG. 2, the FK506-bound affinity resin of the present invention prepared without specifying the binding position on FK506 in Example 2 (lane 3) was confirmed as binding to FKBP12 like the standard affinity resin prepared in Reference Production Example 3 (having a spacer bound thereto at a known position where the binding to FKBP12 is not affected). Regarding the binding to other proteins that bind to FK506, very similar results were obtained for the FK506-bound affinity resin of the present invention prepared in Example 2 and the standard affinity resin prepared in Reference Production Example 3.

These results demonstrate that the method of the present invention is effective and useful.

Example 5

Binding Experiment 2

A binding experiment was conducted in the same manner as Example 4 using the FK506-bound affinity resin prepared in Example 3 and the conventional FK506-bound affinity resin prepared in Reference Production Example 3, which had proven to be effective. The results are shown in FIG. 3.

Figure 3:
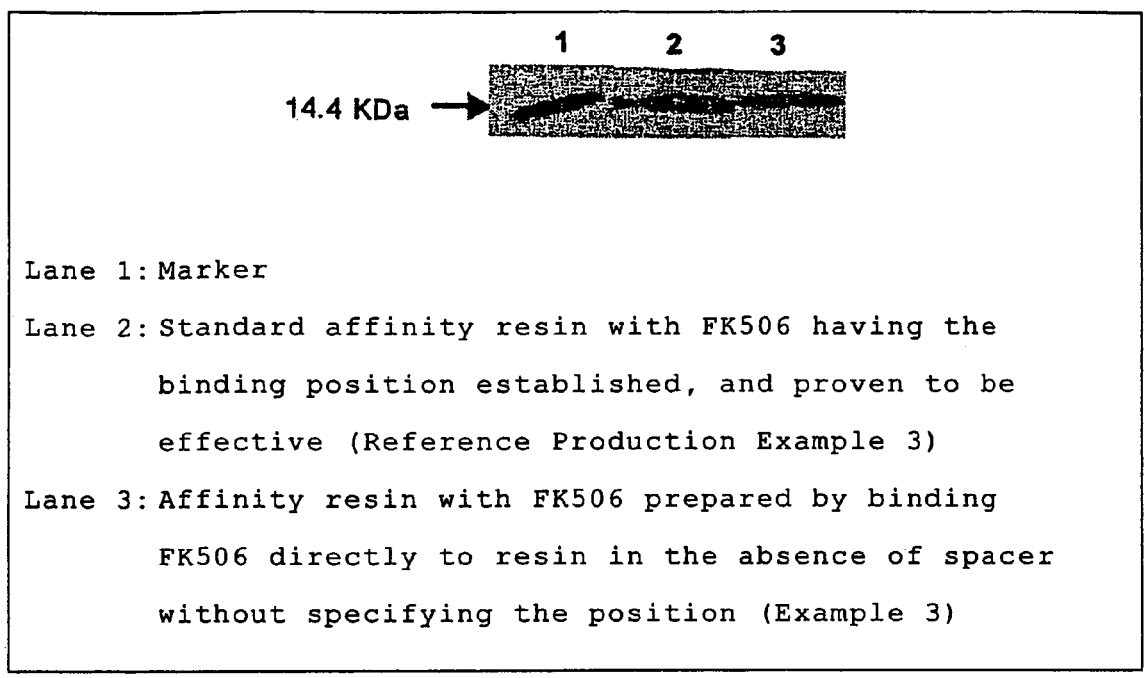
FIG. 3 is an electrophoretogram showing the results of detection of an FK506-binding protein (FKBP12) in a lysate using an FK506-bound affinity resin of the present invention (Example 3).
Lane 1: Marker
Lane 2: Standard affinity resin with FK506 having the binding position established, and proven to be effective (Reference Production Example 3)
Lane 3: Affinity resin with FK506 prepared by binding FK506 directly to resin in the absence of spacer without specifying the position (Example 3)

As seen from FIG. 3, the FK506-bound affinity resin of the present invention prepared by binding FK506 to the solid phase without specifying the binding position in Example 3 was confirmed as binding to FKBP12 like the standard affinity resin prepared in Reference Production Example 3. Regarding the binding to other proteins that bind to FK506, very similar results were obtained for the FK506-bound affinity resin of the present invention prepared in Example 3 and the standard affinity resin prepared in Reference Production Example 3. These results demonstrate that the method of the present invention is effective and useful.

Example 6

FK506-immobilized Solid Phase Support (Activation Treatment of Functional Group)

17-Allyl-1,14-di-hydroxy-12-[2-(4-hydroxy-3-methoxy-cyclohexyl)-1-methyl-vinyl]-23,25-dimethoxy-13,19,21,27-tetramethyl-11,28-dioxa-4-aza-tricyclo[22.3.1.0$^{4,9}$]octacos-18-ene-2,3,10,16-tetraone (FK506; 8.04 mg, 0.01 mmol) was dissolved in acetonitrile ($CH_3CN$; 100 µl), a solution of phosgene ($COCl_2$) in toluene (1.24 mmol/ml; 8 µl, 0.01 mmol) was added at room temperature, and this was followed by stirring for 1.5 hours. After the reaction solution was concentrated under reduced pressure, TOYO-Pearl resin (TSKgel AF-amino, 100 µl, free amino group (available amino group) 0.01 mmol; manufactured by Tosoh Corporation) and acetonitrile ($CH_3CN$; 500 µl) were added, and this was followed by stirring at room temperature for 1.5 hours. After completion of the reaction, the resin was washed with DMF two times and with water two times, a saturated aqueous solution of sodium hydrogen carbonate (1 ml) was added, and this was followed by stirring for 1 minute. After the resin was washed with water two times and with DMF two times, acetic anhydride (100 µl) and DMF (400 µl) were added, and this was followed by stirring at room temperature for 5 minutes. Subsequently, the resin was washed with DMF three times and with 20% aqueous ethanol two times, and the TOYO Pearl resin with FK506 obtained was used in the binding experiment described below.

Example 7

Binding Experiment 3

(1) Preparation of Lysate

The rat brain (2.0 g) was mixed in a buffer A (Tris-HCl containing 0.5% Tween 20 and 300 μM sodium N,N-diethyldithiocarbamate trihydrate, pH 8.0, 20 ml) and prepared as a homogenate, which was then treated by ultrasonic disruption for 10 minutes. The homogenate was centrifuged at 9000 rpm for 10 minutes. The centrifugal supernatant was collected and further centrifuged at 50000 rpm for 30 minutes. The supernatant thus obtained was used as the lysate. Note that the experiment was conducted at 4° C. or on ice throughout the entire time course.

(2) After being thoroughly washed with buffer A, the FK506-bound affinity resin prepared in Example 6 (10 μl) was mixed with the rat brain lysate prepared in (1) above (1 ml), and this was followed by gentle shaking at 4° C. for about 0.5 hours. Centrifugation was conducted, and the supernatant was removed. The FK506-bound affinity resin obtained was thoroughly washed with buffer A, and 25 μl of a loading buffer for SDS (nacalai cat. NO=30566-22, sample buffer solution with 2-ME (2-mercaptoethanol) for electrophoresis, (2×) for SDS PAGE) was added; this was followed by stirring at 25° C. for 10 minutes. The sample solution thus obtained was separated using a commercially available SDS gel (BioRad ReadyGel J, 15% SDS, cat. NO=161-J341); as a result, a band of FKBP12, which is considered to bind specifically onto the resin, was observed.

Example 8

Introduction of Functional Group (use of S-9 Mix)
S-9 Mix: Frozen S-9 Mix for Ames Test (Kikkoman Corporation) was Used

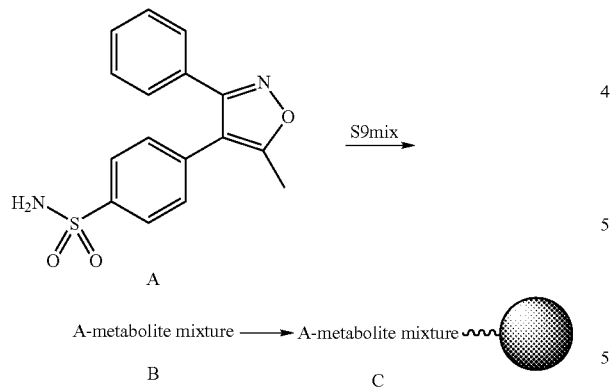

Experimental procedures: 20 ml of S-9 Mix was added to a 50-ml Falcon tube, and a compound A (1.5 mg, 5 μM) dissolved in 75 μl of methanol was added to the S-9 Mix. This mixture was stirred in a constant-temperature chamber at 37° C. for 21 hours. After 3 ml of ethyl acetate was added, the reaction solution was vigorously shaken, then centrifuged at 6,000G for 15 minutes, and the organic phase was separated. Extraction with ethyl acetate was conducted three times. The ethyl acetate phase obtained was washed with saturated saline, and the organic phase was transferred to another Falcon tube (15-ml container) and dried by blowing gaseous nitrogen.

[Immobilization Onto Resin]

A metabolite obtained using S-9 mix (A-metabolite mixture (B)) was dissolved in a mixed solvent of 300 μl of $CH_2Cl_2$ and 30 μl of DMF, and this solution was added to a 0.5-ml Eppendorf tube. Succinic anhydride (0.98 mg, $9.8 \times 10^{-3}$ mmol), triethylamine ($Et_3N$, 0.98 mg, $9.8 \times 10^{-3}$ mmol), and a catalytic amount of DMAP were added, and this was followed by stirring at room temperature for 3.5 hours. 1N HCl (500 μl) was added, and the mixture was extracted with three 1-ml portions of ethyl acetate. The ethyl acetate phase obtained was washed with 500 μl of saturated saline and dried over anhydrous sodium sulfate. The ethyl acetate phase was transferred to a 15-ml conical tube and dried by blowing gaseous nitrogen. To TOYO-Pearl (AF-Amino-650M) (80 μl, 8 μmol), the previously obtained compound dissolved in $CH_2Cl_2$ (1 ml) was added. Benzotriazol-1-yloxytripyrrolidinophosphonium (PyBOP; 5 mg, 9.6 μmol) and diisopropylethylamine (2.5 μl, 19.2 μmol) were added, and this was followed by stirring at room temperature for 17 hours.

After the resin was washed with DMF five times and with $CH_2Cl_2$ five times, 1 ml of a 20% solution of acetic anhydride in $CH_2Cl_2$ was added, this was followed by stirring for 30 minutes, and the amino groups remaining on the resin were subjected to acetyl capping. After the resin was again washed with DMF five times and with $CH_2Cl_2$ five times, it was further washed with a 20% alcohol solution five times to yield the desired resin (C).

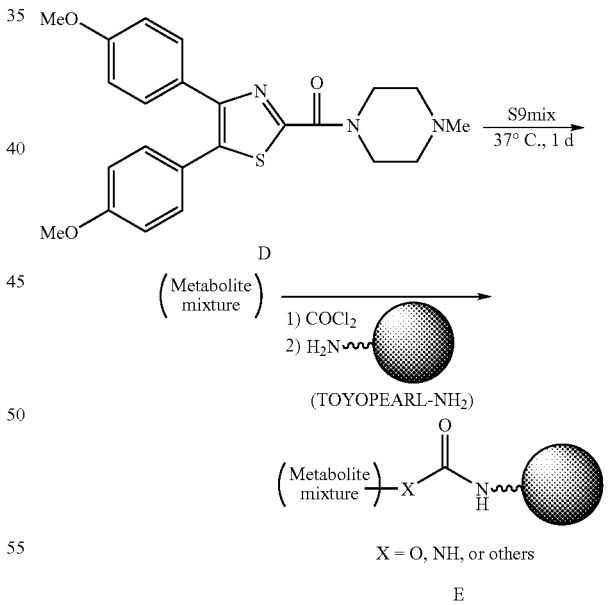

Experimental procedures: 10 ml of S-9 Mix was added to a 50-ml Falcon tube, and a compound D (3.0 mg) dissolved in 75 μl of methanol and 75 μl of water was added to the S-9 Mix. The mixture was stirred in a constant-temperature chamber at 37° C. overnight. After 3 ml of ethyl acetate was added to the reaction solution, the organic phase was separated and extracted. Extraction with ethyl acetate was conducted three times. The ethyl acetate phase obtained was washed with saturated saline, and the organic phase was transferred to another Falcon tube (15-ml container) and dried by blowing gaseous nitrogen. Acetonitrile (500 μl) was added.thereto, and 53 μl of a separately prepared solution of phosgene in toluene (1.24 mmol) was added. This mixture was stirred at room temperature for about 3 hours and concentrated under reduced pressure for several minutes to remove the unreacted phosgene, after which TOYO-Pearl (AF-Amino-650M) (65 μl, 6.5 μmol) was added thereto. This mixture was stirred for several hours and thoroughly washed with acetonitrile, a saturated aqueous solution of NaHCO₃, and water, to yield the desired resin (E).

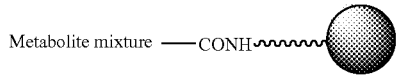

[Binding Experiment]

(1) Preparation of Lysate

After preliminary cultivation, *Escherichia coli* strain DH5α was subjected to main cultivation using SB medium at 37° C. and 130 rpm overnight. After completion of the cultivation, cells were harvested, 10 ml of buffer A was added, and this was followed by homogenization treatment with ultrasound, to yield an *E. coli* lysate (1.5 mg/ml).

One milliliter of the *E. coli* lysate (1.5 mg/ml) was prepared by the addition of 10 μg of COX1 (cyclooxygenase 1; ovine, cayman cat no.60100).

(2) Binding Experiment

Using the S-9-Mix-metabolite-immobilized affinity resin obtained above, a lysate binding experiment was conducted per the following procedures. The lysate used was 1 ml of the lysate prepared above (containing COX1). The amount of S-9-Mix-metabolite-immobilized resin (C) used was 10 μl (equivalent to 1 μmol).

The S-9-Mix-metabolite-immobilized resin (C) and 1 ml of the lysate were gently shaken at 4° C. overnight. The resin was precipitated by centrifugation at 12,000G, and the supernatant was removed. The resin was washed with buffer A five times. To the thus-obtained S-9-Mix-metabolite-immobilized resin (C), 20 μl of a loading buffer for SDS (nakalai cat. NO; 30566-22, sample buffer solution with 2-ME (2-mercaptoethanol) for electrophoresis, (2×) for SDS PAGE) was added; this was followed by stirring at 25° C. for 10 minutes. The thus-obtained sample solution and the reference standard COX1 (cayman cat no.60100) were separated using a commercially available SDS gel (PAG Mini "DAIICHI" 10 (13 W), cat. No.30161), and the SDS gel was analyzed. As a result, a band corresponding to COX1 was detected in the sample solution; it was confirmed that COX1 was bound to the S-9-Mix-metabolite-immobilized resin. Thus, the desired COX1 was successfully extracted from the mixed lysate.

INDUSTRIAL APPLICABILITY

According to the method of the present invention, it is possible to immobilize a ligand to a solid phase support without the need of a previous investigation of structure-activity correlation, which has conventionally been essential, and hence to reduce great deals of labor and costs. Therefore, it is possible to obtain a large number of ligand target molecules in shorter times compared to the conventional method.

This application is based on a patent application No. 319099/2002 filed in Japan, the contents of which are hereby incorporated by reference.

The invention claimed is:

1. A mixture comprising:
    a first solid phase support bound to a first molecule designated molecule A, and
    a second solid phase support bound to a second molecule A at a different position on the second molecule A than that bound to the first solid phase support;
    wherein said mixture is prepared by binding each solid phase support to molecule A without specifying the binding portion on molecule A to the solid phase support, but where each of the solid phase supports is bound to molecule A at a different position on molecule A,
    wherein the first and second solid phase supports are not bound to the same individual molecule A.

2. The mixture of claim 1, wherein the binding of each molecule A to each solid phase support is conducted via a spacer introduced between the first molecule A and the first solid phase support and a second molecule A and the second solid phase support without specifying the introduction position on the molecule A side.

3. The mixture of claim 1, wherein (1) the binding of each molecule A to each solid phase support is conducted via a functional group introduced to each molecule A, and (2) the introduction of the functional group is conducted without specifying the introduction position on the molecule A side.

4. The mixture of claim 2, wherein the introduction of the spacer to each molecule A is conducted via a functional group introduced without specifying the introduction position on the molecule A side.

5. The mixture of claim 3, wherein the introduction of the functional group to each molecule A without specifying the introduction position on the molecule A side is based on a chemical reaction or an enzymatic reaction.

6. The mixture of claim 5, wherein the introduction of the functional group to each molecule A without specifying the introduction position on the molecule A side is based on an enzymatic reaction.

7. The mixture of claim 6, wherein the enzymatic reaction is conducted using a metabolic enzyme.

8. The mixture of claim 4, wherein the introduction of the functional group to each molecule A without specifying the introduction position on the molecule A side is based on a chemical reaction or an enzymatic reaction.

9. The mixture of any one of claims 1-7 or 8 wherein molecule A is a ligand for affinity chromatography.

10. The mixture of claim 1, wherein molecule A is FK506.

11. The mixture of claim 1, wherein molecule A is a steroid hormone.

12. The mixture of claim 1, wherein molecule is an anticancer agent.

13. The mixture of claim 1, further comprising at least one other solid phase support bound to another molecule A at a position on molecule A different from that bound to the first and second solid phase supports, wherein said third solid phase support is not bound to the same individual molecules A bound by the first or second solid phase supports.

14. A mixture comprising:
    ligand molecules of the same type each independently bound to at least one solid phase support via first position on each ligand molecule, and ligand molecules of the same type independently bound to the at least one solid phase support via at least one position, different than said first position, on the ligand molecules;

wherein said ligand molecules when not bound to a solid phase support bind to a target molecule.

15. A mixture comprising:

ligand molecule of a single type each independently bound to a first solid phase support via a first position on each ligand molecule, and ligand molecules of a single type each independently bound to a second solid phase support via at least one position, different than said first position, on the ligand molecules;

wherein said ligand molecules when not bound to a solid phase support bind to a target molecule.

\* \* \* \* \*